(12) United States Patent
Rinne et al.

(10) Patent No.: US 7,949,477 B2
(45) Date of Patent: May 24, 2011

(54) METHOD FOR MONITORING AN ARRANGEMENT FOR DETERMINING THE CONCENTRATION OF AN ANALYTE IN A BODY FLUID

(75) Inventors: Helmut Rinne, Hamburg (DE); Gregor Ocvirk, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/342,346

(22) Filed: Dec. 23, 2008

(65) Prior Publication Data

US 2009/0157330 A1    Jun. 18, 2009

Related U.S. Application Data

(63) Continuation of application No. PCT/EP2007/056208, filed on Jun. 21, 2007.

(30) Foreign Application Priority Data

Jun. 28, 2006   (EP) ..................................... 06116245

(51) Int. Cl.
G06F 19/00    (2011.01)
(52) U.S. Cl. ................ 702/23; 702/45; 702/50; 702/57; 604/31; 604/65; 604/66; 604/6.09; 600/395; 600/396; 600/366; 600/316; 600/365; 210/434; 210/321.65; 210/321.72; 210/929
(58) Field of Classification Search .................... 702/22, 702/23, 30, 31, 32, 50, 45, 57; 604/65, 66, 604/67, 31, 6.09; 600/418, 419, 454, 468, 600/465, 504, 395, 396, 366, 316, 365; 210/87, 210/93, 739, 646, 434, 321.65, 321.72, 929
See application file for complete search history.

(56) References Cited

U.S. PATENT DOCUMENTS

| | | | | |
|---|---|---|---|---|
| 4,464,172 A | * | 8/1984 | Lichtenstein | 604/65 |
| 4,832,034 A | | 5/1989 | Pizziconi et al. | |
| 5,282,950 A | | 2/1994 | Dietze et al. | |
| 5,640,954 A | * | 6/1997 | Pfeiffer et al. | 600/345 |
| 6,063,051 A | * | 5/2000 | Stern | 604/27 |
| 7,205,701 B2 | * | 4/2007 | Liu et al. | 310/313 R |
| 2006/0157413 A1 | * | 7/2006 | Bene et al. | 210/646 |

FOREIGN PATENT DOCUMENTS

| | | |
|---|---|---|
| DE | 44 05 149 | 9/1994 |
| EP | 0 523 463 | 1/1993 |
| EP | 0 722 288 | 7/1996 |
| WO | WO 97/35511 | 10/1997 |
| WO | WO 03/098165 | 11/2003 |

* cited by examiner

Primary Examiner — Carol S Tsai
(74) Attorney, Agent, or Firm — Bose McKinney & Evans LLP

(57) ABSTRACT

The invention relates to a method for monitoring an arrangement for determining a concentration of an analyte in a body fluid. The determination of the concentration of the analyte by means of the arrangement involves a procedure in which the analyte from the body fluid passes through an interface and is transported in a stream of liquid into a flowmeter chamber, in which a measurement is carried out to determine the concentration of the analyte. The evaluation of the measurement takes place in a signal processor. The monitoring of the arrangement comprises the following steps: measurement of measured values of at least two correlated system parameters of the arrangement by means of a sensor system, and comparison of the measured values with limit values stored for each of the system parameters in a storage unit, to obtain a combination of at least two comparison results.

9 Claims, 5 Drawing Sheets

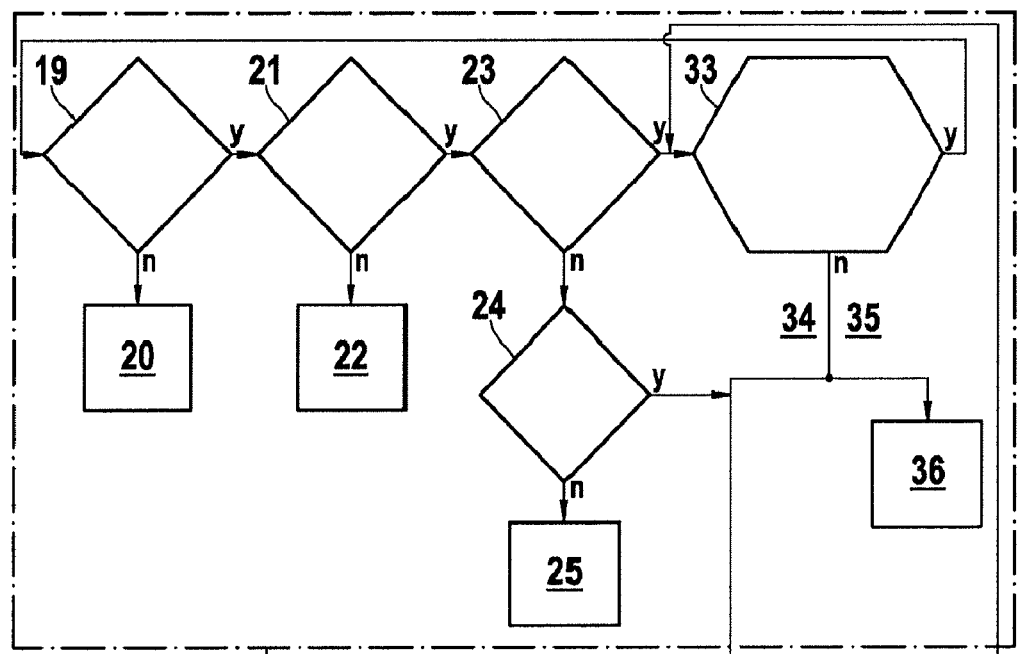
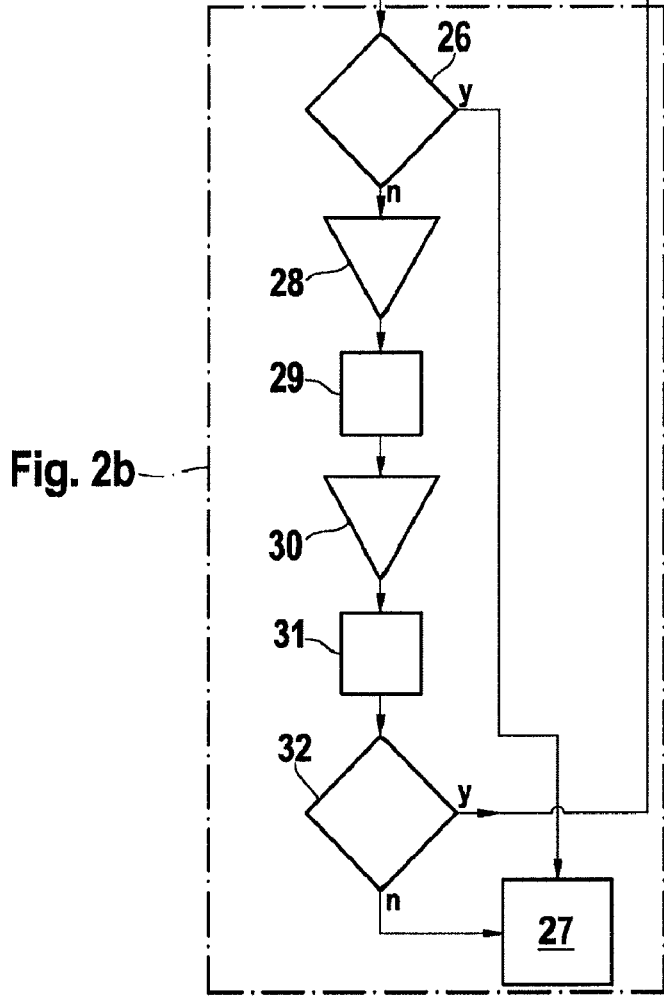
Fig. 2a
Fig. 2b
Fig. 2

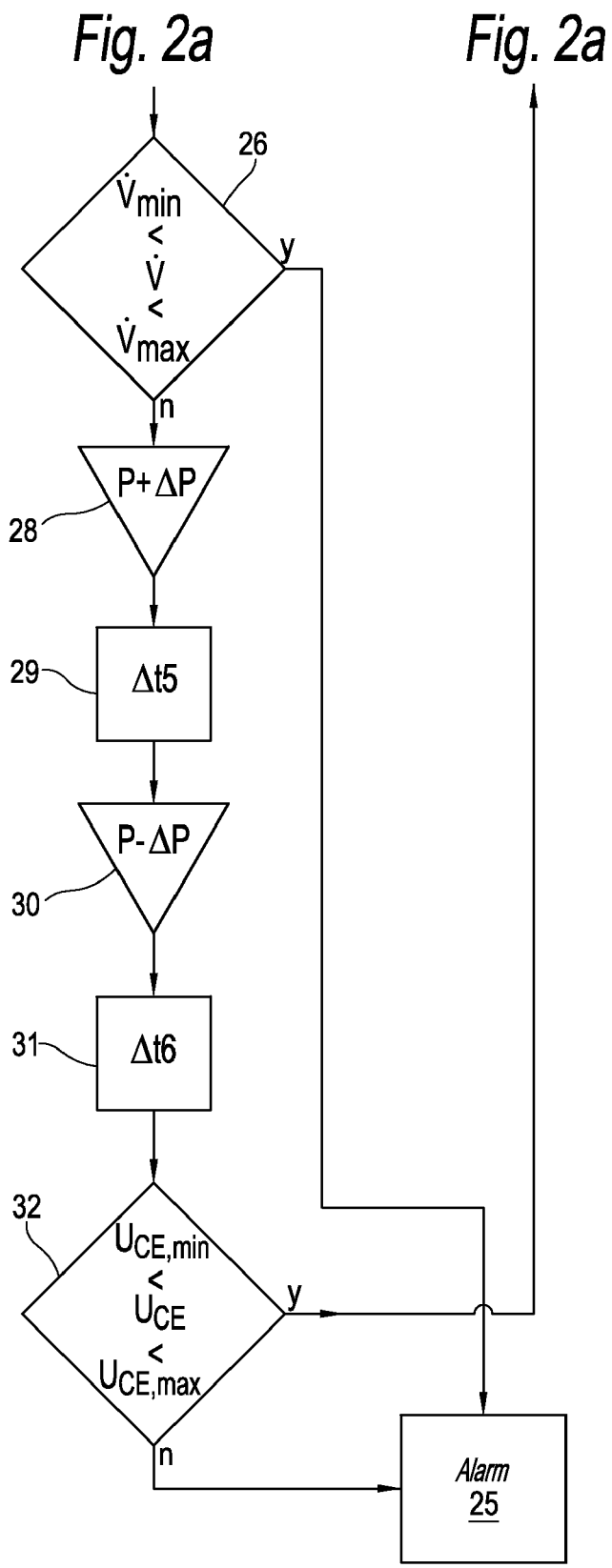

METHOD FOR MONITORING AN ARRANGEMENT FOR DETERMINING THE CONCENTRATION OF AN ANALYTE IN A BODY FLUID

REFERENCE

This application is a continuation of PCT/EP2007/056208 filed Jun. 21, 2007 which is based on and claims priority to European Patent Application No. EP 06 116 245.9 filed Jun. 28, 2006, which are hereby incorporated by reference.

FIELD

The invention relates to a method for monitoring an arrangement for determining the concentration of an analyte in a body fluid in the body of a living human or animal, and to such an arrangement with corresponding monitoring means.

BACKGROUND

Arrangements of this kind are used in the prior art, for example, for monitoring glucose concentration in human blood. EP 0 722 288 relates to a method and a device for monitoring the concentration of a selected substance or a selected group of substances in a body fluid in the body of a living human or animal. The substance or group of substances to be monitored is conveyed out of the body through an interface and is transported away from the reverse side of the interface in a stream of perfusion liquid. The concentration of the substance or group of substances to be monitored is measured in the perfusion liquid downstream from the interface, the rate of flow of the stream of perfusion liquid being less than 60 µl/h.

DE 44 05 149 relates to an arrangement for determining the concentration of constituents in body fluids using a dialysis probe which can be implanted in body tissue and through which a perfusion solution flows, the inflow end of the dialysis probe being connected via a pump to a perfusion solution reservoir and the return flow end being connected to a collecting container via at least one enzyme cell serving as a sensor for the substance concentration. The enzyme cell output is connected to an extracorporeal evaluation/display unit. The perfusion solution reservoir, the pump, the enzyme cell and the collecting container are combined, separately from the evaluation/display unit, as a sensor unit in their own first housing. The dialysis probe, the perfusion solution reservoir, the pump, the enzyme cell and the collecting container are combined, separately from the evaluation/display unit, as a probe/sensor unit in their own second housing.

In such arrangements known in the prior art, a great many malfunctions can occur that have negative impacts on measurement accuracy. An incorrectly determined concentration value of the analyte can, however, have serious consequences for the person who is using the arrangement and who, for example, is controlling the administration of insulin as a function of the glucose concentration value that is determined. Consequently, reliable monitoring of the arrangement for determining the concentration of the analyte is necessary.

SUMMARY

The present invention avoids the disadvantages of the prior art and, in particular, provides a method for reliable monitoring of an arrangement for determining the concentration of an analyte in a body fluid.

The present invention provides a method for monitoring an arrangement for determining a concentration of an analyte in a body fluid, in which the determination of the concentration of the analyte by means of the arrangement involves a procedure in which the analyte from the body fluid passes through an interface and is transported in a stream of liquid into a flowmeter chamber, in which a measurement is carried out to determine the concentration of the analyte, and an evaluation of the measurement takes place in a signal processor. The monitoring of the arrangement comprises the following steps: measurement of measured values of at least two correlated system parameters of the arrangement by means of a sensor system, and comparison of the measured values with limit values stored for each of the system parameters in a storage unit, to obtain a combination of at least two comparison results.

The arrangement to be monitored comprises an interface through which the analyte (for example, glucose) can pass from the body fluid (for example, blood or interstitial fluid) into the arrangement. The body fluid, in which the concentration of the analyte is determined by the arrangement, can be in direct contact with the interface, or the concentration in the body fluid can be calculated indirectly from the concentration of the analyte in the liquid in contact with the interface. The interface is, for example, a semipermeable membrane in a microdialysis probe that is introduced subcutaneously into the tissue of a body. The semipermeable membrane separates the interstitial space from the interior of the probe and permits the diffusion of the analyte from the interstitial fluid into a perfusion liquid in the interior of the probe. However, the interface of the arrangement that is to be monitored can be in the form of any desired interface that allows the analyte to pass into the arrangement, in particular also an open window.

The analyte that has passed through the interface is transported in a stream of liquid (stream of perfusion liquid/stream of dialysate) into a flowmeter chamber. The perfusion liquid (for example, an isotonic analyte-free liquid) is preferably transported by a transport device (in particular a pump, for example, a micro-mechanical diaphragm pump or a roller pump) from a reservoir to the interface and, together with the analyte contained in it, from the interface to a flowmeter chamber via a liquid conduit.

In the flowmeter chamber, a measurement takes place to determine the concentration of the analyte. For this purpose, a detector arrangement is contained in the flowmeter chamber. The detector arrangement is advantageously designed as an amperometric detector arrangement. Amperometry is an electrochemical method based on a current measurement at constant potential. To this end, the "three electrodes method" known in the art and a potentiostat are preferably used.

To determine the glucose concentration in a fluid, the enzyme glucose oxidase, for example, is used to convert the glucose into hydrogen peroxide, among other things. The hydrogen peroxide formed serves as a detector molecule and is oxidized on a working electrode included in the detector arrangement, and the electric current thus generated is detected. For this purpose, a three-electrode measurement arrangement is used, consisting of a working electrode, a counterelectrode and a reference electrode, i.e., an electrode of constant electrochemical potential. The potential between working electrode and reference electrode, required for the desired reaction, is set by regulation of the current between working electrode and counter-electrode by the potentiostat.

The measurement carried out by the detector arrangement in the flowmeter chamber (for example, the measured current generated during the oxidation of the hydrogen peroxide on the working electrode) is evaluated by means of a signal processor contained in the arrangement. The signal processor determines, from the measured values of the detector arrangement, the concentration of the analyte in the body fluid. The fluid used up is preferably transported from the flowmeter chamber into a collecting container in the arrangement and is stored in said collecting container.

A malfunction of such an arrangement for determining the concentration of an analyte in a body fluid can have an effect on a large number of system parameters. The expression "system parameters" relates, in the context of the invention, to parameters that depend on the actual state of the arrangement and influence its functionality, in particular, the accuracy of the measured values determined by the arrangement. Examples of system parameters are the temperature of the stream of liquid flowing through the flowmeter chamber, the electrical voltage between the working electrode and counterelectrode and between the working electrode and reference electrode of a detector arrangement present in the flowmeter chamber, the flow rate of the perfusion liquid through the flowmeter chamber, pump parameters of a pump provided for pumping the perfusion liquid along the interface and through the flowmeter chamber, for example, the electric current of the pump and the speed of the pump, the battery voltage of a battery provided for supply of energy to the arrangement, and the active membrane exchange surface of a membrane provided as interface.

To identify a malfunction of the arrangement in good time and to avoid dangers resulting therefrom (for example, the administration of too high or too low a dose of insulin to a diabetic), the arrangement is monitored by means of the method according to the invention.

For monitoring the arrangement, a sensor system is provided in the arrangement. According to the invention, measured values of at least two correlated system parameters of the arrangement are measured by means of this sensor system. In this context, correlated system parameters are system parameters whose values are linked.

According to exemplary embodiments of the invention, the measured values of the at least two correlated system parameters are compared with limit values stored for each of the at least two parameters in a storage unit of the arrangement (preferably with comparison of two or three correlated system parameters). The limit values can define, for each system parameter, an upper limit and/or a lower limit. Conceivable comparison results for each system parameter are then: the measured value of the system parameter lies above the upper limit; the measured value lies below the upper limit; the measured value lies below the upper limit and above the lower limit; or the measured value lies above the lower limit, or the measured value lies below the lower limit.

The comparison of the measured values of the at least two correlated system parameters with the limit values yields a certain combination of comparison results. For example, the measured values of two correlated system parameters could yield the following combination of two comparison results: (1) the measured value of the first system parameter lies above a defined upper limit; and (2) the measured value of the second system parameter lies between a defined lower limit and a defined upper limit.

A specific state of the arrangement can be assigned to this combination of at least two comparison results. States that can be assigned to certain combinations of comparison results are states of the arrangement that affect its functionality. States can be assigned that are expressed in the combination of the measured system parameters. Possible states that can be assigned to the arrangement are preferably selected from the following group: that the correct function of the arrangement is ensured; that the efficiency of a component of the arrangement is reduced; that a certain defect of the arrangement is detected; or that an unknown defect of the arrangement exists.

The evidence of the measurements of the at least two correlated system parameters together permits a detection of the state of the arrangement, in particular of certain defects of the arrangement, which is not permitted by measurement of one system parameter alone. A reliable and continuous monitoring of the functionality of the arrangement is thus made possible by the method according to the invention.

The invention further relates to an arrangement for determining a concentration of an analyte in a body fluid, comprising an interface for taking the analyte from a body fluid into a stream of perfusion liquid in the arrangement, a liquid conduit for routing the stream of liquid from the interface to a flowmeter chamber, a transport device for transporting the stream of liquid through the liquid conduit from the interface to the flowmeter chamber, a detector arrangement located in the flowmeter chamber and used to carry out measurements to determine the concentration of the analyte, and a signal processor for calculating the concentration of the analyte from results of the measurement by the detector arrangement. The signal processor is preferably configured such that it can accept a reference value and compute it for calibration. The arrangement moreover may contain a sensor system for measurement of measured values of at least two (in particular, at least three) correlated system parameters, a storage unit, and means (in particular, a processor) for comparing the measured values with limit values stored for each of the system parameters in the storage unit, to obtain a combination of at least two (in particular, at least three) comparison results.

This arrangement can be used to carry out the method according to the invention. During use, the arrangement can be arranged outside the body of a living human or animal, except for the interface (for example, a microdialysis probe with semipermeable membrane) and, if appropriate, a small part of the liquid conduits extending to the interface and away from the interface. In particular, the monitoring method is performed exclusively outside the body. For this purpose, the sensors of the sensor system are arranged upstream of, downstream of and/or in the flowmeter chamber. The entire arrangement can be substantially miniaturized and constitutes a portable arrangement. Preferably, the sensor system comprises at least two sensors selected from the following group: electrical voltage sensor, electric current sensor, temperature sensor, flow rate sensor, revolution counter and concentration sensor. The concentration sensor is provided in particular for measuring the change in concentration of a substance exchange marker.

The concentration of the analyte can be determined by electrochemistry and amperometry, the measurement sensor comprising a polarizable electrode arrangement disposed in a flowmeter chamber. This electrode arrangement can consist, for example, of a working electrode made of platinum, a counterelectrode made of silver or platinum, and a reference electrode made of silver or silver/silver chloride.

According to one embodiment of the present invention, the signal processor, with defined combinations of comparison results, triggers at least one reaction of the arrangement, the at least one reaction being selected from the following group: display of a warning or problem report by a display unit of the arrangement, display of a recalibration prompt by the display unit, display, by the display unit, of a prompt to replace a component of the arrangement, switching off of the arrangement, output of an optical, acoustic or haptic alarm signal, regulation of at least one system parameter, influencing of values of a first system parameter by regulation of the values of a second system parameter correlated with the first system parameter, brief modification of a system parameter in order to eliminate a possible system error as a result of the combination of the comparison results.

The arrangement may comprise a display unit (for example, a liquid crystal display) which, in addition to warnings, can also display, for example, concentration values determined by the arrangement, or user menus from which a user is able to select user menu items, for example, by means of a keypad or other form of operating unit. With certain combinations of comparison results, the display unit can display warnings which, for example, warn a user of a defect of the arrangement or of resulting incorrect determination of a concentration value. For example, in the case of the following combination of comparison results: a) the measured value of the countervoltage (first system parameter) between counterelectrode and working electrode lies outside a range defined for this system parameter by an upper limit and a lower limit; b) the temperature of the stream of liquid (second system parameter correlated with the first system parameter) lies below a defined upper limit and above a defined lower limit; and c) the flow rate through the flowmeter chamber (third system parameter correlated with the first system parameter) lies below a defined upper limit and above a defined lower limit the display unit preferably displays a warning of a system error.

Moreover, with defined combinations of comparison results (in particular, those combinations pointing to a defect of the arrangement), the arrangement can output an optical alarm signal (for example, flashing of an LED), an acoustic alarm signal (for example, a warning tone) and/or a haptic alarm signal (for example, vibration of a component of the arrangement).

Another possible reaction of the arrangement to certain combinations of comparison results is the display, by the display unit, of a recalibration prompt. A recalibration can be carried out by directly measuring the concentration of the analyte in a collected sample of the body fluid and inputting this directly measured concentration value into the arrangement as a calibration value. Such a calibration is necessary, for example, if a defective state of the arrangement, which leads to an inadmissibly high measurement error, cannot be converted, by regulation of a system parameter, to a fault-free state that results in an admissibly high measurement error. Another possible reaction of the arrangement to certain combinations of comparison results is the display, by the display device, of a prompt to replace a component of the arrangement. For example, the user can be prompted to replace a battery.

Furthermore, the reaction to a defined combination of comparison results can be the regulation of a system parameter and/or the influencing of values of a first system parameter by regulation of the values of a second system parameter correlated with the first system parameter. For this purpose, regulating means are provided in the arrangement according to the invention. For example, the flow rate lying below the limit value can be regulated with the aid of the pump speed. Unsuccessful regulation results in a changed sensitivity of the current/concentration curve, such that, for example, a recalibration prompt is made.

Moreover, the signal processor can in certain cases cause the arrangement to switch off. For example, the signal processor can cause the arrangement to switch off if, after a temporary increase in the pumping rate, the mean flow rate measured over one hour falls below the stored limit value for the flow rate.

Another possible reaction of the arrangement to certain combinations of comparison results is a brief modification of a system parameter in order to eliminate a possible system error on account of the combination of the comparison results. For example, in the following combination of comparison results a) the measured value of the flow rate lies below a defined lower limit, b) the measured value of the battery voltage lies above a defined lower limit, and c) the measured value of a pump variable (for example, the speed of the pump) is below a defined upper limit, the pump variable (for example, the speed of the pump) can be increased briefly (for a defined time interval $\Delta t$), in order to flush away a flow obstruction possibly present in the conduits for the perfusion liquid. After the time interval has elapsed, the pump variable is lowered again, and a flow rate measured value is detected again and compared with the limit values defined for the flow rate.

In a method according to one embodiment of the invention, the sensor system preferably carries out measurements for the determination of at least two system parameters selected from the following group: temperature of the stream of liquid, electrical voltage between at least two electrodes along which the stream of liquid flows in the flowmeter chamber, time change of an electric current in relation to the time change of an electrical voltage with reference to at least two electrodes arranged in the flowmeter chamber, system variable of a transport device which is contained in the arrangement and which serves to transport the stream of liquid, battery voltage of at least one battery provided for energy supply in the arrangement, flow rate of the stream of liquid through the flowmeter chamber, and concentration of a marker.

The temperature of the stream of liquid can, for example, be measured directly by means of a temperature sensor which is positioned in the stream of liquid directly upstream of, in or directly downstream of the flowmeter chamber. However, it can also be recorded indirectly by a temperature measurement, by means of the temperature sensor, in which the temperature sensor measures the temperature of a structural part that is in direct or indirect contact with the stream of liquid. The electrochemical reaction taking place in an electrochemical flowmeter chamber for determination of the concentration of analytes is dependent on the temperature of the perfusion liquid (dialysate) in the flowmeter chamber, among other reasons because of the temperature dependency of the substance transport of analytes, reactants and reaction products from and to the electrode and the rate constants of the reaction itself. Therefore, if the temperature dependency of the measurement signal is known, it is possible, for example, on the one hand, to measure the temperature and to compensate mathematically for temperature fluctuations that occur, or, on the other hand, to minimize the temperature fluctuations by thermostating.

The electrical voltage between a counterelectrode and a working electrode (countervoltage) and/or between a reference electrode and a working electrode (cell voltage) can be determined, the counterelectrode, reference electrode and working electrode being provided for measuring the concentration of an analyte (for example, glucose). The cell voltage applied for the electrochemical reaction of the analyte is to be selected such that the measured current of the electrochemical reaction can be attributed as far as possible to the reaction of the analyte on the working electrode, i.e., that the reaction can be kept as free of interference as possible. For this purpose, it is necessary for the cell voltage to be maintained as constant as possible during the operation of the arrangement.

A transport device contained in the arrangement, and used to transport the perfusion liquid, is, for example, a pump that can be designed as a diaphragm pump (e.g., with piezoelectric drive), a piston pump (e.g., syringe pump), a dynamic pump (e.g., hydrodynamic or electro-osmotic pump) or as a hose pump. System variables of a pump are, for example, the electric current of the pump or the speed of the pump.

The at least one battery (or one accumulator) provided in the arrangement is used, for example, for supply of energy to an electrically operated pump, provided as transport device for the perfusion liquid, to a display unit, to a signal processor and to other components of the arrangement according to the invention.

To determine the flow rate of the stream of liquid through the flowmeter chamber, a flow rate sensor can be provided which is positioned, for example, downstream from the flowmeter chamber. The cross-membrane diffusive transport of substance in a (microdialysis) catheter is subject to a nonlinear dependency of the flow rate. Moreover, in an amperometric flowmeter chamber, a sensor signal dependent on flow rate can be established at constant analyte concentration. Finally, the flow rate has a direct effect on the time delay between the enrichment of the analyte in the perfusate and the measurement of the analyte concentration in the ex vivo flowmeter chamber (dead time). In view of these relationships, it is desirable for the system flow rate to be maintained as constant as possible. Within the technically acceptable tolerances of the system flow rate, the system flow rate is also to be selected such that a slight change in the system flow rate results in only slight changes of the measurement signal.

Moreover, the concentration of a marker in the stream of liquid can be determined in order to indicate the cross-membrane diffusive transport of substance at the interface of the arrangement (if a membrane is present). For a given perfusion liquid and temperature, the cross-membrane diffusive flux is dependent on the flow rate through a conduit (catheter) along the membrane and on the membrane exchange surface. The variation of the membrane exchange surface in vivo can be determined by determining the concentration of an endogenous marker, for example, sodium ions, present at an almost constant concentration. The cross-membrane diffusive flux of the analyte can be mathematically determined from this such that, for example, the flow rate can be adjusted in order to increase the diffusive flux.

Two correlated system parameters within the meaning of the present invention are in particular: a) the flow rate and the battery voltage (since, when the battery voltage drops, the capacity of the pump and thus the flow rate drop); b) the flow rate and a system variable of the transport device (since a system variable of the transport device directly influences the flow rate); c) the battery voltage and a system variable of the transport device (see comments for a) and b); d) the countervoltage and the temperature of the perfusion liquid (as the temperature increases, the turnover increases and, consequently, the countervoltage required to obtain a constant cell voltage increases); e) the countervoltage and the flow rate (as the flow rate increases, the electrochemical turnover per unit of time in the flowmeter chamber drops and the countervoltage therefore also drops); and f) the ratio of the time change of the electric measured current in the flowmeter chamber to the time change of the counter voltage and the flow rate (when the ratio lies below a certain limit value, there is a suspicion of the working electrode being coated with particles or an air bubble, which in turn has a negative impact on the flow rate).

According to an exemplary embodiment of the present invention, when carrying out the monitoring method according to the invention, a countervoltage between a counterelectrode, arranged in the flowmeter chamber, and a working electrode, a temperature of the stream of liquid, and a flow rate of the stream of liquid through the flowmeter chamber, are in each case compared by the signal processor with limit values stored in the storage unit.

According to a preferred embodiment of the present invention, when carrying out the monitoring method according to the invention, a flow rate of the stream of liquid through the flowmeter chamber, a battery voltage of a battery contained in the arrangement, and a system variable of a transport device contained in the arrangement and used to transport the stream of (perfusion) liquid, are in each case compared by the signal processor with limit values stored in the storage unit.

Values of at least one system variable measured by the sensor system can be taken into account in the determination of the concentration of the analyte. For example, the temperature of the stream of liquid can be measured by means of a temperature sensor, and a compensation value can then be determined from the measured temperature value. The temperature dependency of the electrode signal for determination of the concentration of the analyte can then be mathematically eliminated by means of the concentration value. Various possible ways of determining the compensation value are known in the prior art.

According to an exemplary embodiment of the present invention, at least two correlated system parameters are continuously monitored by the sensor system, while the determination of the concentration of the analyte typically takes place continuously. The measurement to determine the concentration of the analyte particularly preferably takes place with a defined measurement frequency, and the determination of the measured values of the at least two correlated system parameters also takes place with this defined measurement frequency. Measured values that are used to determine the concentration of the analyte can thus be attributed directly to values of the system parameters.

According to an exemplary embodiment, the method according to the invention is used to monitor an arrangement for determining the concentration of glucose in a body fluid, particularly in blood, of a live human. This arrangement can be used to determine the concentration of glucose in a body fluid of a live human.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawing, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
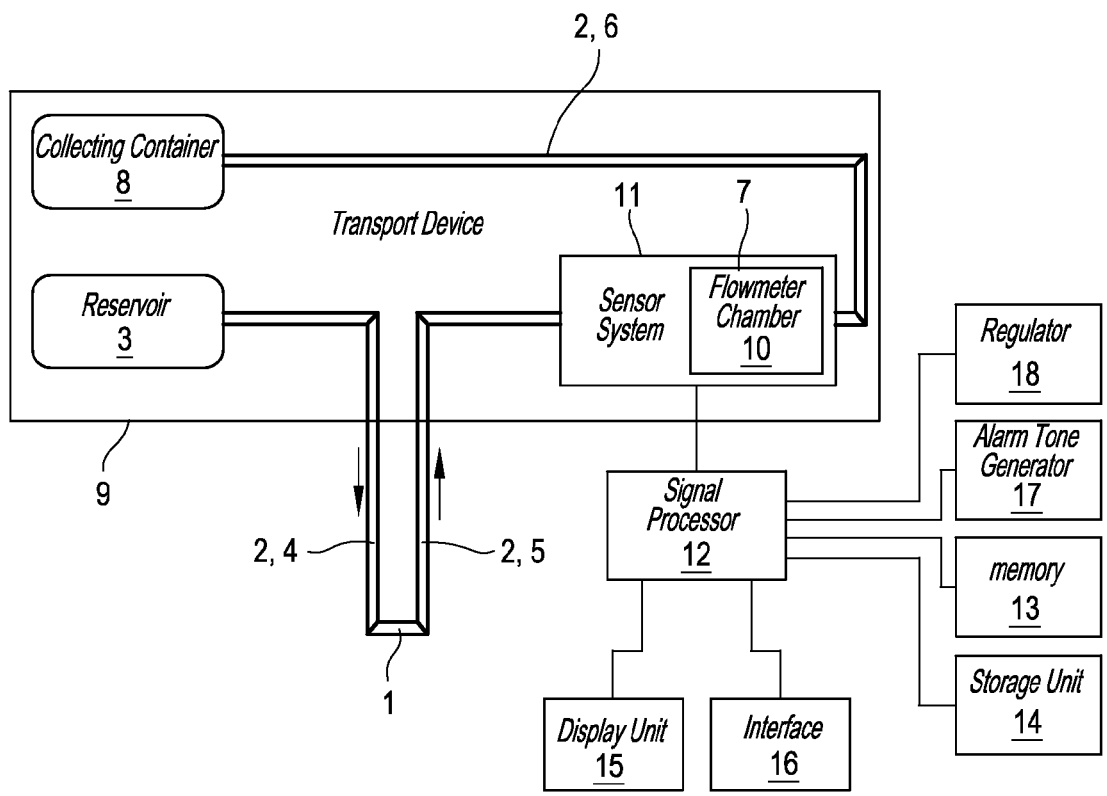
FIG. 1 shows a schematic representation of an arrangement according to the invention.

FIG. 1 is a schematic representation of the components of an arrangement according to the invention for determination of a concentration of an analyte in a body fluid. The arrangement comprises an interface 1, for example, a microdialysis probe, via which an analyte (for example, glucose) from a body fluid (for example, interstitial fluid) can pass into a stream of liquid 2 in the arrangement (sample collection). The perfusion liquid is pumped from a reservoir 3 through a first liquid conduit 4 to the interface 1 and from there through a second liquid conduit 5, a flowmeter chamber 10 and a third liquid conduit 6 into a collecting container 8. A transport device 9 is provided for pumping the liquid. In the flowmeter chamber 10 there is a detector arrangement 7 (for example, a three-electrodes system containing a reference electrode, a working electrode and a counterelectrode with a potentiostat), which is used to carry out measurements for determining the concentration of the analyte. In the area of the flowmeter chamber 10, there is a sensor system 11, which is used to measure values of at least two correlated system parameters. The sensor system 11 and the detector arrangement 7 are connected to a signal processor 12. From the results of the measurements by the detector arrangement 7, the signal processor 12 calculates (if appropriate taking into account a calibration value) the concentration of the analyte. The relationships between the measurement signal, the concentration of the analyte in the stream of liquid 2, the concentration of the analyte in the body fluid with which the interface 1 is in contact (for example, interstitial fluid) and, if appropriate, the concentration of the analyte in another body fluid (for example, blood) are known in the prior art and are stored in the signal processor 12, preferably in the form of calculation rules.

The signal processor 12 is connected to a memory 13 in which, for example, measured or calculated values can be stored. Moreover, a further storage unit 14 can be provided which contains reference values for comparison with the measured values of the sensor system 11. The reference values stored in the further storage unit 14 can be limit values for the at least two determined system parameters, for which purpose the memory 13 can also be used. The signal processor 12 serves as a means for comparing the actual values of the at least two correlated system parameters with these limit values stored in the storage unit 14. This in each case yields an actual combination of at least two comparison results. With defined combinations of comparison results, the signal processor 12 triggers a reaction of the arrangement. The reaction, for example, involves a display unit 15 displaying a warning (for example, of a heightened measurement error of the detector arrangement 7), a problem report, a recalibration prompt, or a prompt to replace a component of the arrangement. By way of an interface 16 (for example, a keypad), a user can, for example, adjust the settings or functions of the arrangement or input a recalibration value. Other possible reactions to an actual combination of at least two comparison results can be the triggering of an alarm tone generator 17, which emits an acoustic alarm signal. Furthermore, a regulator 18 can be activated, for example, for regulating a system parameter such as the cell voltage or the flow rate. Such a regulator has the advantage that the arrangement can operate over a long period of time without intervention by the user.

FIG. 2 shows a flow chart of a first embodiment of a monitoring method according to the invention.

This monitoring method is used to monitor the sensor voltages and currents of an amperometric detector arrangement. The cell voltage (polarization voltage) between the working electrode and the reference electrode is monitored by a comparison 19 of mean cell voltage values $\bar{U}_{pol}$, determined from measured values of a voltage sensor of the sensor system, with limit values $\bar{U}_{polmin}$ and $\bar{U}_{polmax}$. If the cell voltage lies outside the range set by the limit values (comparison result n), it must be assumed that there is a problem with the arrangement or with the coupling between arrangement and voltage sensor. Consequently, an alarm is triggered/a warning report displayed 20 in order to prompt a trained user to eliminate the problem.

If the comparison 19 reveals that the cell voltage values lie within the range set by the limit values (comparison result y), the battery voltage $U_{BATT}$ is checked. The battery voltage measured by a voltage sensor of the sensor system is compared with a lower limit value $U_{BATT,min}$ (reference number 21). If the battery voltage lies below the limit value (comparison result n), an alarm is triggered/a report displayed 22, in order to prompt the user to change the battery.

If the comparison 21 reveals that the battery voltage values lie above the lower limit value (comparison result y), the countervoltage $U_{CE}$ between the counterelectrode and working electrode of the detector arrangement is checked. For this purpose, the countervoltage measured by a voltage sensor of the sensor system is compared with lower and upper limit values $U_{CEmin}$ and $U_{CEmax}$ (reference number 23). If the countervoltage lies outside the range defined by the limit values (comparison result n), then the temperature T correlated with the countervoltage is checked by a comparison 24 with lower and upper limit values $T_{min}$ and $T_{max}$. If the temperature measured by a temperature sensor of the sensor system lies outside the range set by the limit values (comparison result n), then the combination of the comparison results for countervoltage and temperature (n, n) reveals that a system error is present and an alarm 25 should be triggered.

If the temperature lies within the range defined by the limit values (comparison result y), then, according to the invention, the mean flow rate F correlated with the countervoltage is checked by comparison 26 with limit values $F_{min}$ and $F_{max}$.

If the mean flow rate F determined from measured values of a flow rate sensor of the sensor system lies within the range set by the limit values (comparison result y), then the combination of the comparison results for countervoltage, temperature and mean flow rate (n, y, y) reveals that a system error is present and an alarm 27 should be triggered.

If the mean flow rate F lies outside the range set by the limit values (comparison result n), then the combination of the comparison results for counter-voltage, temperature and mean flow rate (n, y, n) reveals that a flow obstruction is possibly leading to at least partial coating of the counterelectrode. Therefore, in order to eliminate this problem, a pump variable P (for example, the electric current of the pump) is increased by ΔP (reference number 28) for a time interval Δt5 in order to increase the flow rate. After Δt5 has elapsed (reference number 29), the pump variable is lowered again by ΔP (reference number 30). Then, after a time interval Δt6 has elapsed (reference number 31), a comparison 32 of the countervoltage $U_{CE}$ with the limit values $U_{CEmin}$ and $U_{CEmax}$ is again carried out.

If the comparison 32 reveals that the countervoltage still lies outside the range defined by the limit values (comparison result n), an alarm 27 is triggered as a reaction. If it now lies within the range (comparison result y), then the ratio of the time change of the measured current dI/dt to the time change of the countervoltage $dU_{CE}/dt$ is next checked by a comparison 33 with lower and upper limit values. This comparison is also carried out if the original comparison 23 of the countervoltage has delivered the comparison result y (countervoltage lying within the limit values). If the ratio of the time change of the measured current to the time change of the counter-voltage lies between the limit values (comparison result y), then the method is carried out again, starting with the comparison 19 of the cell voltage. If the ratio lies outside the range set by the limit values, a distinction is made between two cases 34, 35. In the first case 34, the lower limit value is undershot. As a reaction to this, the method, as described above, is continued by checking the flow rate (comparison 26). In the second case 35, the upper limit value is exceeded and, as a reaction, the arrangement is switched off 36, since a short circuit is suspected.

Figure 2A:
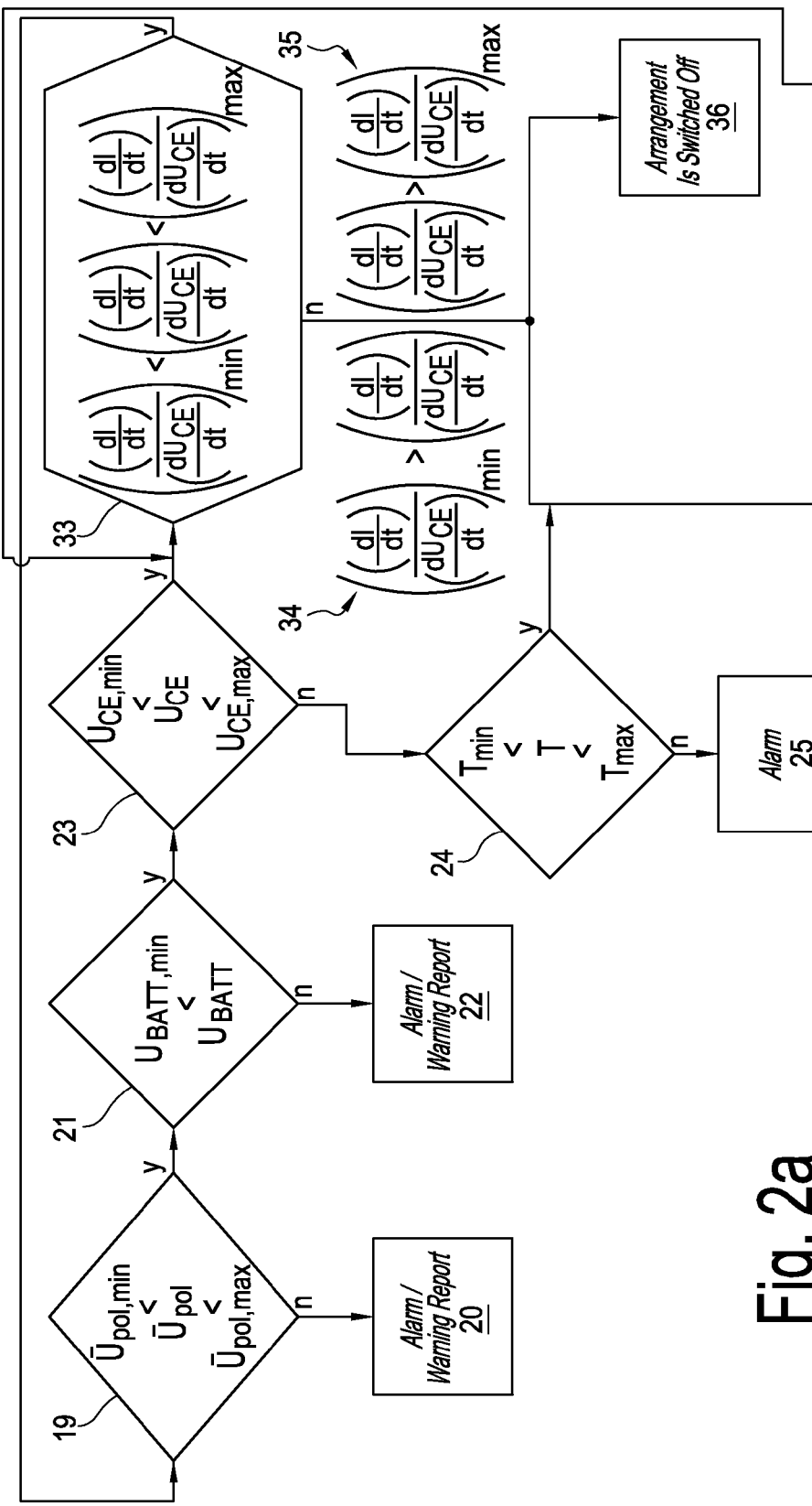
FIG. 2 shows a flow chart of a first embodiment of a monitoring method according to the invention.

FIG. 2 is shown enlarged, with further inscriptions, in both subsidiary FIGS. 2a and 2b.

Figure 3:
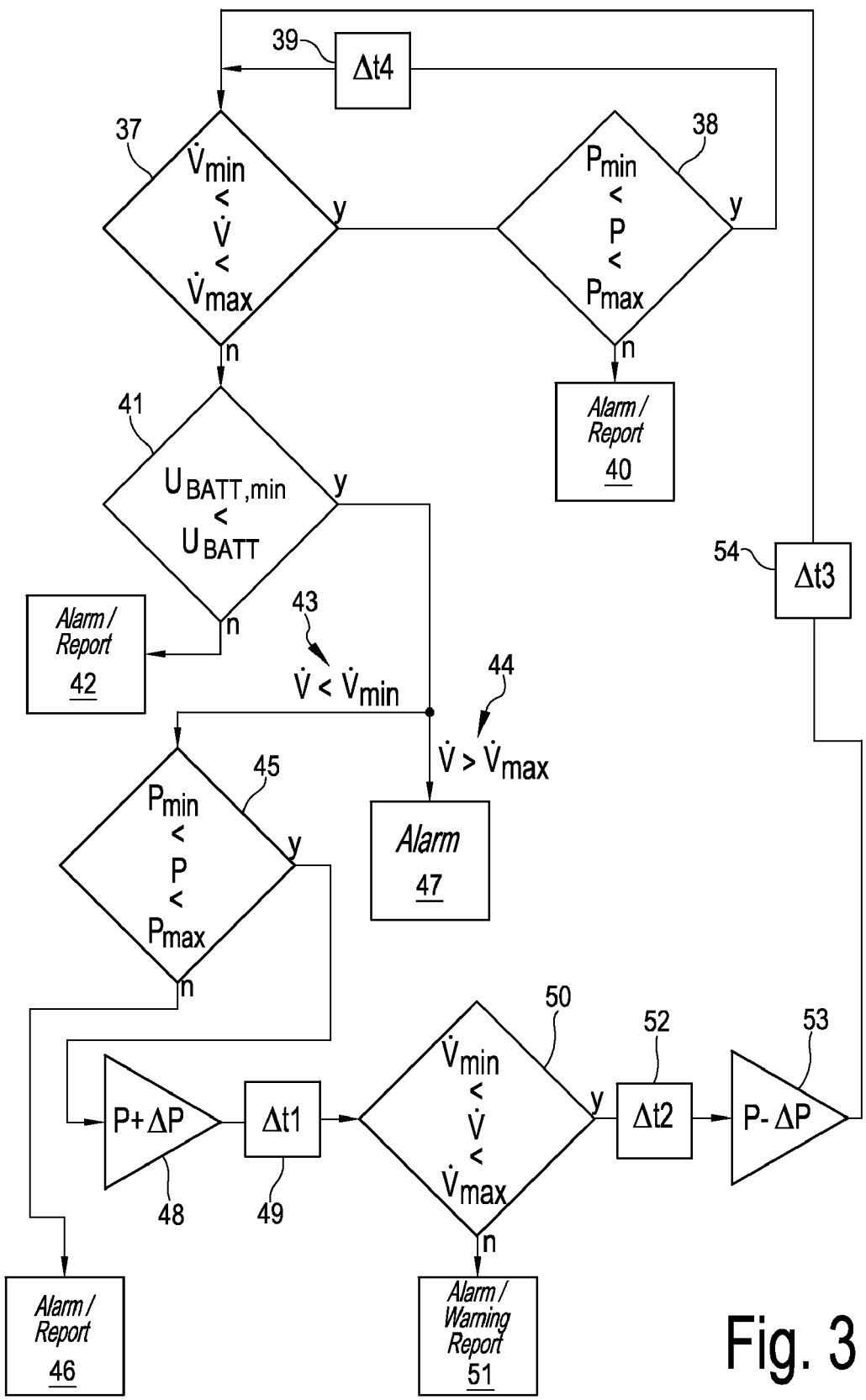
FIG. 3 shows a flow chart of a second embodiment of a monitoring method according to the invention.

FIG. 3 shows a flow chart of a second embodiment of a monitoring method according to the invention.

The embodiments according to FIGS. 2 and 3 can be implemented singly or in combination in an arrangement according to the invention (for example, according to FIG. 1). The monitoring method according to FIG. 3 is used to monitor the flow rate in an arrangement for determining the concentration of an analyte.

The constancy of the flow rate of a stream of liquid is an important condition for a constant dead time, a constant substance exchange via the interface (for example, membrane wall of a catheter) and the concentration measurement in the flowmeter chamber (for example, electrochemical measurement). The mean flow rate is therefore preferably monitored by a comparison 37 of a flow rate F, determined from measured values of a flow rate sensor, with lower and upper limit values $F_{min}$ and $F_{max}$. If the flow rate lies within the range defined by the limit values (comparison result y), then the pump variable P correlated with the flow rate is checked by a comparison 38 with lower and upper limit values $P_{min}$ and $P_{max}$ in order to test the transport device (pump). In the case of a pump variable lying between the limit values (comparison result y), the combination of the comparison results of flow rate and pump variables (y, y) reveals that the transport device (pump) is functioning correctly. The comparison 37 of the actual flow rate with the limit values is then repeated after a time interval $\Delta t4$ (reference number 39).

In the case of a pump variable lying outside the range defined by the limit values in the comparison 38 (comparison result n) (for example, if the current consumption of the pump is too high), an alarm is triggered/a report displayed 40, in order to prompt a user to check the pump.

If the comparison 37 of the mean flow rate reveals that it lies outside the range set by the limit values (comparison result n), then the battery voltage $U_{BATT}$ correlated with the mean flow rate is checked. It is compared for this purpose with a lower limit value $U_{BATT,min}$ (reference number 41). If the battery voltage drops below the limit value (comparison result n), then an alarm or a message 42 prompts the user to replace the battery or accumulator. If the battery voltage lies above the limit value (comparison result y), then a distinction is made between two cases 43, 44 for this combination of comparison results of flow rate and battery voltage (n, y).

In the first case 43, the mean flow rate lies below the lower limit value $F_{min}$. In this case, the pump variable P correlated with the flow rate (for example, the pump current or speed) is checked by comparison 45 with limit values $P_{min}$ and $P_{max}$. If the pump variable lies outside the range set by the limit values (comparison result n), then the combination of the comparison results for mean flow rate, battery voltage and pump variable (n, y, n) reveals that there is a defect of the transport device (pump), such that an alarm is triggered/a report displayed 46 in order to prompt the user to check the pump.

If the pump variable lies within the range defined by the limit values (comparison result y in comparison 45), then the combination of the comparison results for mean flow rate, battery voltage and pump variables (n, y, y) reveals that a bubble or a particle may be forming a temporary flow obstruction. In order to eliminate this problem, the pump variable P (for example, the pump current) is increased by $\Delta P$ (reference number 48) for a time interval $\Delta t1$ in order to increase the flow rate. After $\Delta t1$ has elapsed (reference number 49), a comparison 50 of the mean flow rate with the limit values $F_{min}$ and $F_{max}$ is carried out again.

If the comparison 50 reveals that the mean flow rate still lies outside the range defined by the limit values (comparison result n), an alarm is triggered as a reaction or a warning report is displayed (reference number 51). If it lies within the range (comparison result y), then the pump variable is lowered again by $\Delta P$ (reference number 53) after a time interval $\Delta t2$ has elapsed (reference number 52). The mean flow rate is then checked again (comparison 37) after a defined time interval $\Delta t3$ has elapsed (reference number 54).

In the second case 44, the mean flow rate lies above the upper limit value $F_{max}$. In this case, an alarm 47 is triggered directly in order to warn of a system error.

Thus, embodiments of the method for monitoring an arrangement for determining the concentration of an analyte in a body fluid are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method for monitoring an arrangement for determining concentration of an analyte in a body fluid, the arrangement having an interface through which the body fluid passes, a flowmeter chamber which receives a stream of the liquid and carries out a measurement to determine concentration of the analyte, and a signal processor which evaluates the measurement, the method comprising the following steps:

using a sensor system to obtain measured values of at least two correlated system parameters of the arrangement;

comparing the measured values with limit values stored for each of the system parameters in a storage unit to obtain at least two comparison results; and determining with the signal processor whether a malfunction has occurred in the arrangement based upon the at least two comparison results.

2. The method of claim 1, wherein, with defined combinations of comparison results, the signal processor triggers at least one reaction of the arrangement, the at least one reaction being selected from the following group: displaying a warning or problem report by a display unit of the arrangement, displaying a recalibration prompt by the display unit, displaying by the display unit a prompt to replace a component of the arrangement, switching off of the arrangement, output of an optical, acoustic or haptic alarm signal, regulation of at least one system parameter, influencing the values of a first system parameter by regulating the values of a second system parameter correlated with the first system parameter, and brief modification of a system parameter in order to eliminate a possible system error on account of the combination of the comparison results.

3. The method of claim 1, wherein the sensor system carries out measurements to determine at least two system parameters selected from the following group: temperature of the stream of liquid, electrical voltage between at least two electrodes along which the stream of liquid flows in the flowmeter chamber, time change of an electric current in relation to a time change of an electrical voltage with reference to at least two electrodes arranged in the flowmeter chamber, system variable of a transport device which is contained in the arrangement and which serves to transport the stream of liquid, battery voltage of at least one battery provided for energy supply in the arrangement, flow rate of the stream of liquid through the flowmeter chamber, and concentration of a marker.

4. The method of claim 1, wherein a countervoltage between a counterelectrode, arranged in the flowmeter chamber, and a working electrode, a temperature of the stream of liquid, and a flow rate of the stream of liquid through the flowmeter chamber, are in each case compared by the signal processor with limit values stored in the storage unit.

5. The method of claim 1, wherein a flow rate of the stream of liquid through the flowmeter chamber, a battery voltage of a battery contained in the arrangement, and a system variable of a transport device contained in the arrangement and used to transport the stream of liquid, are each compared by the signal processor with respective limit values stored in the storage unit.

6. The method of claim 1, wherein the values of at least one system variable measured by the sensor system are taken into account in the determination of the concentration of the analyte.

7. The method of claim 1, wherein the measurement to determine the concentration of the analyte takes place with a defined measurement frequency, and the measurement of the measured values of the at least two correlated system parameters also takes place with the defined measurement frequency.

8. An arrangement for determining a concentration of an analyte in a body fluid, comprising:
   an interface for taking an analyte from a body fluid into a stream of perfusion liquid in the arrangement;
   a liquid conduit for routing the stream of perfusion liquid from the interface to a flowmeter chamber;
   a transport device for transporting the stream of liquid from the interface to the flowmeter chamber;
   a detector arrangement located in the flowmeter chamber and used to carry out measurements to determine the concentration of the analyte;
   a signal processor for calculating the concentration of the analyte from results of the measurements by the detector arrangement;
   a sensor system for obtaining measured values of at least two correlated system parameters;
   a storage unit; and
   means for comparing the measured values with limit values stored for each of the system parameters in the storage unit, to obtain a combination of at least two comparison results.

9. The arrangement of claim 8, wherein the sensor system comprises at least two sensors selected from the following group: electrical voltage sensor, electric current sensor, temperature sensor, flow rate sensor, revolution counter and concentration sensor.

* * * * *